United States Patent
Dreyfuss et al.

(10) Patent No.: US 10,492,776 B2
(45) Date of Patent: Dec. 3, 2019

(54) KNOTLESS REPAIR TECHNIQUE USING TAPE/SUTURE HYBRID

(71) Applicant: Arthrex, Inc., Naples, FL (US)

(72) Inventors: Peter J. Dreyfuss, Naples, FL (US); Derek C. Sullivan, Bonita Springs, FL (US); Tara L. Swanlaw, Estero, FL (US)

(73) Assignee: Arthrex, Inc., Naples, FL (US)

( * ) Notice: Subject to any disclaimer, the term of this patent is extended or adjusted under 35 U.S.C. 154(b) by 386 days.

(21) Appl. No.: 15/602,846

(22) Filed: May 23, 2017

(65) Prior Publication Data

US 2017/0252033 A1 Sep. 7, 2017

Related U.S. Application Data

(62) Division of application No. 14/198,102, filed on Mar. 5, 2014, now Pat. No. 9,687,222.

(Continued)

(51) Int. Cl.
*A61B 17/04* (2006.01)
*A61F 2/08* (2006.01)
*A61B 17/06* (2006.01)

(52) U.S. Cl.
CPC ...... *A61B 17/0401* (2013.01); *A61B 17/0487* (2013.01); *A61B 17/06166* (2013.01); *A61F 2/0811* (2013.01); *A61B 2017/0403* (2013.01); *A61B 2017/0427* (2013.01); *A61B 2017/0445* (2013.01); *A61F 2002/0829* (2013.01); *A61F 2002/0852* (2013.01);
(Continued)

(58) Field of Classification Search
CPC ............ A61B 17/0401; A61B 17/0487; A61B 17/06166; A61B 2017/0445; A61B 2017/0427; A61B 2017/0403; A61B 2017/0409; A61B 2017/0411; A61B 2017/0412; A61B 2017/0414; A61B 2017/0432; A61B 2017/043; A61B 2017/0464; A61B 2017/045; A61F 2002/0829; A61F 2002/0852; A61F 2002/0864; A61F 2002/0888; A61F 2002/0817; A61F 2250/0036; A61F 2/0811

See application file for complete search history.

(56) References Cited

U.S. PATENT DOCUMENTS 6,716,234 B2 4/2004 Grafton et al.
7,329,272 B2 2/2008 Burkhart et al.
(Continued)

FOREIGN PATENT DOCUMENTS

EP 2572648 A1 3/2013

*Primary Examiner* — Erich G Herbermann
(74) *Attorney, Agent, or Firm* — Blank Rome LLP

(57) ABSTRACT

Systems and methods for soft tissue to bone repairs, without knot tying. The soft tissue repair systems include self-cinching constructs with a fixation device, a flexible construct having a flexible strand abutting a suture tape, and a shuttle/pull device attached to the flexible strand and provided within the body of the fixation device. A splice is formed by pulling on the shuttle/pull device subsequent to the fixation device being secured into the bone, to allow the wide tape to be positioned over the tissue (for best compression and minimum tissue cut-thru) and suture for the implanted portion (for most efficient and least bone removal).

9 Claims, 2 Drawing Sheets

Related U.S. Application Data

(60) Provisional application No. 61/772,823, filed on Mar. 5, 2013.

(52) U.S. Cl.
CPC ............. *A61F 2002/0864* (2013.01); *A61F 2002/0888* (2013.01); *A61F 2250/0036* (2013.01)

(56) References Cited

U.S. PATENT DOCUMENTS

| | | |
|---|---|---|
| 7,892,256 B2 | 2/2011 | Grafton et al. |
| 8,439,976 B2 | 5/2013 | Albertorio et al. |
| 8,460,379 B2 | 6/2013 | Albertorio et al. |
| 8,821,543 B2 | 9/2014 | Hernandez |
| 2005/0192631 A1* | 9/2005 | Grafton ............ A61B 17/06166 606/228 |
| 2008/0004659 A1 | 1/2008 | Burkhart et al. |
| 2008/0255613 A1* | 10/2008 | Kaiser ................ A61B 17/0401 606/232 |
| 2010/0160962 A1 | 6/2010 | Dreyfuss |
| 2013/0023928 A1 | 1/2013 | Dreyfuss |
| 2013/0085528 A1* | 4/2013 | DiMatteo ........... A61B 17/0401 606/232 |
| 2013/0096611 A1 | 4/2013 | Sullivan |

\* cited by examiner

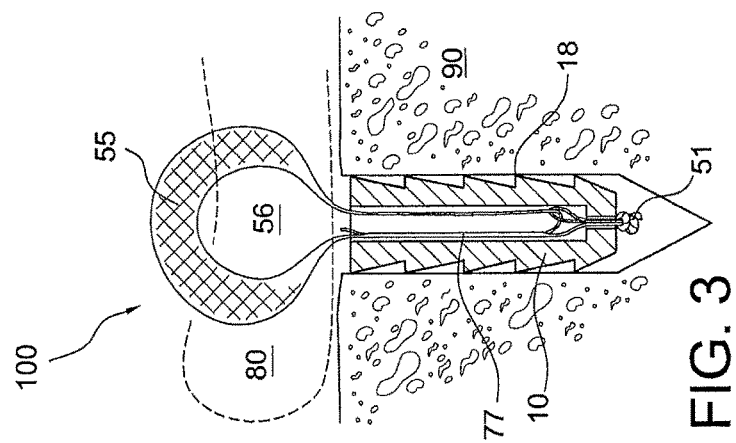
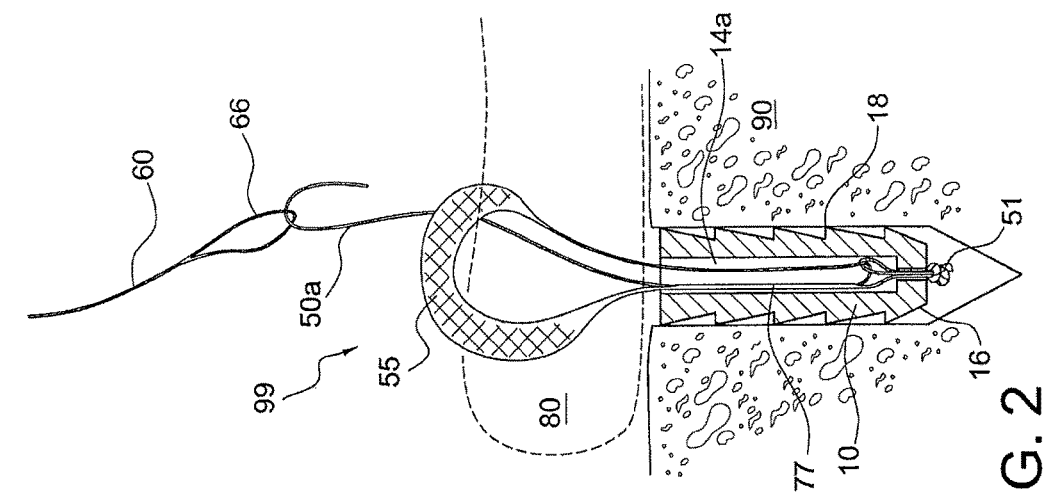
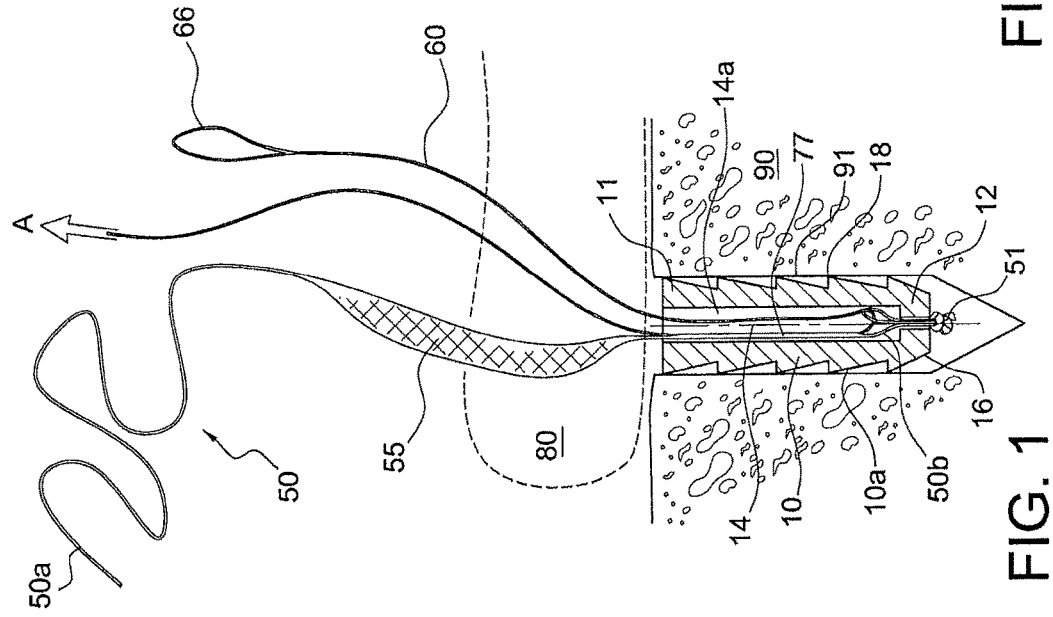

KNOTLESS REPAIR TECHNIQUE USING TAPE/SUTURE HYBRID

CROSS-REFERENCE TO RELATED APPLICATIONS

This is a divisional of U.S. patent application Ser. No. 14/198,102, filed Mar. 5, 2014, which claims the benefit of U.S. Provisional Application No. 61/772,823, filed Mar. 5, 2013, the disclosures of which are incorporated by reference in their entireties herein.

FIELD OF THE INVENTION

The present invention relates to surgical devices and, in particular, to a knotless tape/suture construct.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

It would be desirable to provide a knotless anchor construct which has a design that allows minimizing both the tissue cut-thru and the amount of bone removed, while maximizing tissue compression. A knotless tensionable fixation device with tape above the bone (to provide maximum tissue fixation and compression) and suture-only below the bone (to allow for small-size fixation devices and minimal amount of bone removed for securing such small size-fixation devices) is also needed. Also needed are improved methods for tissue fixation with a knotless fixation device with tape above the bone (preferably only tape above the bone) and suture-only below the bone.

SUMMARY OF THE INVENTION

The present invention provides a knotless construct for fixation of soft tissue to bone with the ability to provide maximum tissue compression with minimal tissue cut-thru and amount of bone removed. The knotless construct is a tape/cord hybrid construct that includes an anchor body with a tape portion (tape region) provided over the tissue to be reconstructed, and a cord (flexible strand) provided in the bone and/or the anchor body.

The present invention also provides a method of knotless tissue repair by providing an anchor where a first end of a flexible strand is fixed and the second end is brought around tissue and fixed in the anchor body in a knotless manner The flexible strand is a cord-like (suture-like) at the ends and tape-like in between the ends. The desired resultant repair has wide tape over tissue (for best compression and minimum tissue cut-thru) and suture for the implanted portion (for most efficient and least bone removal).

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 1-3 illustrate subsequent steps of a method of knotless tissue fixation with a tape/suture construct (anchor) of the present invention.

DETAILED DESCRIPTION OF THE PREFERRED EMBODIMENTS

Figure 4:
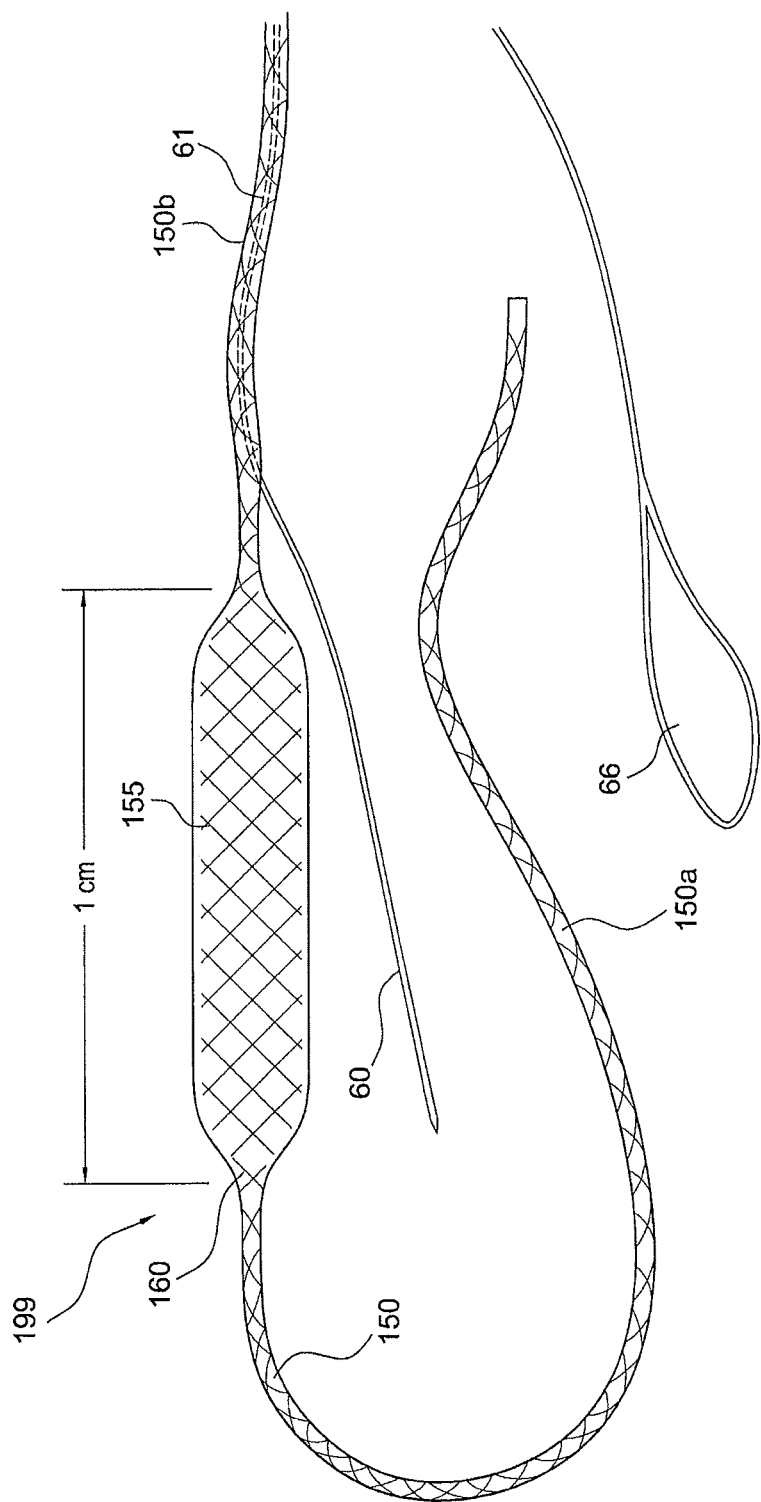
FIG. 4 illustrates a schematic view of another surgical construct (anchor) of the present invention.

The present invention provides surgical systems and methods for knotless ligament repair and fixation, such as fixation of soft tissue to bone. The knotless construct of the present invention is a knotless anchor that comprises an anchor body and at least a flexible hybrid tape/cord attached to the body. In an exemplary embodiment, the knotless construct is a tape/suture construct that comprises an anchor body with a tape portion (tape region) provided over the tissue to be reconstructed or reapproximated, and a cord or suture portion (suture region) provided in the bone and/or the anchor body.

The present invention also provides a knotless fixation device with tape above the bone (preferably only tape above the bone, to provide maximum tissue fixation and compression) and cord-only (suture-only) below the bone (to allow for small-size fixation devices and minimal amount of bone removed for securing such small size-fixation devices).

In an exemplary embodiment, the flexible strand has first and second ends that abut a middle portion (a wide portion or tape portion) with a width/diameter larger than the width/diameter of the first and second ends. The wide portion (tape portion) may have same composition and/or properties as those of the first and second ends, or different ones. Preferably, the flexible strand is in the form of a suture construct having the same number of suture yarns but with a flat wider middle portion to resemble a tape-like suture. In additional embodiments, the flat wider middle portion may have more yarns than the ends or may have fewer yarns than the ends.

The present invention also provides a method of knotless tissue repair by providing an anchor where a first end of a flexible material/strand is fixed and the second end is brought around tissue and fixed in the anchor body in a knotless manner. The flexible material/strand is a cord-like (suture-like) at the ends and tape-like in between the ends. The desired resultant repair has wide tape over tissue (for best compression and minimum tissue cut-thru) and suture for the implanted portion (for most efficient and least bone removal).

Referring now to the drawings, where like elements are designated by like reference numerals, FIGS. 1-3 illustrate surgical system 100 of the present invention for repairing tissue, for example, for approximating soft tissue 80 to bone 90. Surgical system 100 is a surgical construct that includes a fixation device 10 and a tensionable construct 99 which is preferably pre-loaded onto the fixation device 10. As detailed below, the tensionable construct 99 is formed of a flexible material (flexible construct) and a shuttling device attached to the flexible material. The flexible material (flexible construct) consists of a flexible strand or cord 50 provided with an integral, flat wider middle portion 55, for example, a tape portion 55. Shuttling device 60 is attached to the flexible strand or cord 50 of the tensionable construct 99 and aids in the formation of a splice within the flexible strand as part of a knotless, self-locking adjustable mechanism, to allow tensioning of the final construct.

Surgical system 100 shown in FIGS. 1-3 is an exemplary tape/suture knotless anchor 100 of the present invention to be secured into bone 90. For simplicity, the surgical system 100 will be described below with reference to a flexible strand or cord 50 in the form of exemplary suture, and a wide middle region 55 in the form of exemplary suture tape. However, the invention is not limited to this exemplary-only embodiment, and contemplates any suture-like or cord-like materials and strands, for example, braided, knitted or woven, or formed of a multi-filament suture without a core to allow easy splicing, or the FiberWire® suture, as long as the middle portion (region) 55 has a width greater than that of the cord or flexible strand 50.

Fixation device 10 of exemplary tape/suture knotless anchor 100 is an anchor or implant 10 provided with an integral cannulated body 10a having a proximal end 11, a distal end 12, a longitudinal axis 14, and at least one flexible strand or cord 50 extending through cannulation 14a of body 10a, as shown in FIGS. 1-3. FIG. 4 illustrates additional details of another exemplary-only embodiment of a flexible strand 150 with tape 155 of the present invention.

Body 10a may have various configurations and geometries such as, for example, a corkscrew configuration with a thread around the central body and having a configuration that facilitates insertion of the anchor into the bone by providing a gradual change from a starting pitch (i.e., a thread disposed along the longitudinal axis of the anchor at the distal end of the anchor) to a helical or spiral pitch around the central body 10a. By providing the starting pitch at the distal end of the anchor, the anchor 10 can be inserted more readily into the bone without the need for additional or excessive force. Body 10a may be threaded or may be a push-in style body, or a ribbed body, as well. For example, FIGS. 1-3 illustrate anchor 10 with a pointed tip 16 and thread 18 to allow easy insertion within a pilot hole or bone hole 91 formed within bone 90.

Fixation device 10 may be also an anchor with a post and a pair of openings symmetrically positioned relative to the post, the pair of openings extending in a direction about transversal to the longitudinal axis of the body, the pair of openings being configured to allow the tensionable construct 99 to be passed through the body of the fixation device and around the post.

Flexible strand 50 shown in FIG. 1 is a strand with two ends and a flat wider middle portion 55. In an exemplary embodiment, flexible strand 50 is a suture with a flat wider middle portion, or a tape with suture ends. The flat wider middle portion may be created by braiding, weaving or knitting or any combination. The suture/tape construct may be also manually assembled. There may be a taper from the flat wider middle portion transitioning to the suture ends (for example, taper 160 illustrated in FIG. 4).

As shown in FIG. 1, flexible strand 50 is provided with first and second ends 50a, 50b and a middle portion 55. At least one of the first and second ends 50a, 50b is formed of suture-like (cord-like) suture, for example, braided, knitted or woven, or formed of a multi-filament suture without a core to allow easy splicing, or the FiberWire® suture (disclosed in U.S. Pat. No. 6,716,234 the disclosure of which is hereby incorporated by reference in its entirety herewith). Preferably, both ends 50a, 50b are formed of suture-like (cord-like) suture. Middle portion (middle region) 55 has a width greater than the width of ends 50a, 50b and may be formed to be flat by braiding, weaving or knitting the middle portion of the flexible strand (to achieve a greater width/ diameter than that of the ends) or by any other method known in the art. Preferably, both ends are formed of suture-like (cord-like) suture.

As shown in FIG. 3, one end (for example, end 50b) is securely attached to the anchor body 10a by being fixed and tied, for example, in a static knot 51 at the distal end 12 of the anchor body 10a. The other end (for example, end 50a) is brought around the tissue (or through tissue) and then secured to the anchor body 10a (fixed to the anchor body) in a knotless manner, and as detailed below.

In an exemplary-only embodiment, end 50a is spliced and passed through itself within the anchor body, to create a construct that is tensionable after insertion in bone (to allow attached tissue to be brought proximate to bone) and does not require tying of any knots. As such, and according to an exemplary-only embodiment, end 50a is secured to the anchor body 10a and knotlessly attached to it by employing a shuttle/pull device 60, for example, a shuttling wire 60 (passing wire 60) with loop 66. The shuttle/pull device 60 is provided pre-attached to the strand 50a and forms a splice subsequent to the insertion of the anchor body 10a within the bone 90 (and subsequent to attachment to soft tissue 80 to be repaired or fixated) to allow formation of the final fixation device with a knotless self-locking mechanism that allows the user (for example, the surgeon) to control the tension of the strand on the soft tissue 80 to be attached to bone 90. The shuttle/pull device 60 may be a shuttle/pull suture device such as a passing instrument, for example, a FiberLink™ or a Nitinol loop.

The shuttle/pull device 60 (shuttling wire 60) is provided attached to flexible strand 50, as shown in FIG. 1. Both the flexible strand 50 and the shuttling device 60 of the tensionable construct 99 extend through the cannulated body 10a of the fixation device 10. The shuttling device 60 is configured to be pulled out of the body of the fixation device to allow the flexible strand to pass through an eyelet 66 of the shuttling device 60 and through itself to form a knotless closed loop having an adjustable length (perimeter) and a splice.

By pulling the shuttling wire 60 in the direction of arrow "A" (FIG. 1), the non-fixed end 50a is brought inside the anchor body 10a to form a splice through itself, for example, splice 77 shown in FIGS. 2 and 3, and loop 56 (FIG. 3) with wide tape-like region 55 around the tissue 80 to be secured. Loop 56 is a knotless, adjustable loop that allows the tissue 80 to achieve the desired compression with maximum footprint.

FIG. 3 illustrates the tape portion 55 forming loop 56 located outside the anchor body 10a to compress tissue 80 to be fixated. Final construct 100 is provided with wide tape 56 (preferably only wide tape) above the bone 90 and around and above soft tissue 80, and with only suture 50 below the bone 90 and below the soft tissue 80.

FIG. 4 illustrates another exemplary-only embodiment of a tensionable construct 199 consisting of flexible strand 150 which has a flat wider middle portion 155 (of about 1 cm long) and two adjacent ends 150a, 150b, and also a shuttling device 60 with an eyelet 66 pre-attached to the flexible end 150b. The construct has a tape-like region 155 which is wider than the rest of the strand but still retains the necessary strength. Taper region 160 is provided at each opposing end of the tape 155. Ends 150a, 150b are preferably coreless sutures to allow easy splicing. Tensionable construct 199 is shown in FIG. 4 before splicing and before the formation of a closed adjustable loop.

A method of tissue fixation and tissue compression according to an exemplary embodiment of the present invention comprises inter alia the steps of: (i) providing a suture/tape anchor construct 100 having a fixation device 10 with a body 10a, a flexible strand 50 with two ends 50a, 50b of suture and a middle portion 55 of wide tape, wherein the first end 50b of the flexible strand 50 is fixed; (ii) passing the second end 50a around or through tissue 80 to be fixated; and (iii) fixing the second end 50a in the body 10a of the fixation device in a knotless manner, to form an adjustable knotless loop 56 extending around or through the tissue 80 to be fixated. The resultant repair has wide tape 55 over tissue 80 (for best compression and minimum tissue cut-thru) and suture 50 for the implanted portion and only within the bone 90 (for most efficient and least bone removal).

Exemplary tape/suture construct 100 described above may be employed for various tissue repairs such as fixation of soft tissue to bone. In an exemplary embodiment only, a pilot hole is created in bone by employing a punch or a drill, for example. After the pilot hole is created and the punch or drill is removed, the tape/suture construct 100 is pre-loaded onto a driver (for example, a standard hand driver). The anchor with driver is inserted into the prepared pilot hole by hand. A mallet may be used to advance the push-in style implant into the hole, or the driver is rotated to advance a screw-in style implant. Once the anchor is advanced into the pilot hole, the driver handle is pulled straight off the anchor. By pulling on the shuttling/pull device 60, the flexible strand 50 forms splice 77 with tape loop 56 located over the tissue to be fixated. In this manner, the final construct 100 is a knotless construct that comprises tape located only above the bone 90 and around soft tissue 80, and suture 50a, 50b located only below the bone 90. Additional details on the formation of splice 77 within anchor body 10 are set forth in U.S. Patent Application Publication No. 2013/0096611, the disclosure of which is incorporated by reference in its entirety herein.

Body 10a may be formed of a bioabsorbable material such as poly(l-lactide-co-d,l-lactide) 70:30 (PLDLA), PEEK, metals or metal alloys (such as stainless steel, titanium or titanium alloys, for example), absorbable and/or nonaborbable materials, natural and/or synthetic polymers, among many others. Although body 10a of construct 100 has been illustrated as having a specific threaded configuration, the invention is not limited to this exemplary only embodiment and contemplates an anchor having different shapes and geometries, or a combination of different shapes and geometries.

Flexible strand or cord 50 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

In a preferred embodiment, the flexible strand 50 may be a high-strength suture, such as an ultrahigh molecular weight polyethylene (UHMWPE) suture which is the preferred material as this material allows easy splicing. The strands may be also formed of a stiff material, or combination of stiff and flexible materials, depending on the intended application. The strands may be also coated and/or provided in different colors. The knotless anchors of the present invention can be used with any type of flexible material or suture that forms a splice and a loop and that is provided with a wider flat tape portion located about the middle of the flexible material.

The tape-like region 55 may be in the form of flat suture tape (for example, a collagen stuffed suture tape or a high strength suture tape, such as disclosed in U.S. Pat. No. 7,892,256) or a combination of suture and tape, a stiff material, or combination of stiff and flexible materials, depending on the intended application. As detailed above, the tape-like region is preferably formed by knitting, weaving or braiding a suture strand (with same or different number of yarns) to provide a wider portion while the construct retains the necessary strength.

The shuttle/pull device may be a shuttle/pull suture device such as a suture passer instrument, for example, FiberLink™ or a Nitinol loop.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others.

The knotless suture constructs also include flexible strands or sutures that are spliced—at least in part—in a manner similar to an Arthrex ACL TightRope®, such as disclosed in U.S. Pat. Nos. 8,439,976 and 8,460,379, the disclosures of which are incorporated by reference in their entirety herein.

Additional constructs may be inserted dependent upon the size of the soft tissue defect. Suture passing and knot tying are carried out in the preferred fashion to secure attachment of soft tissue to bone.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A method of tissue repair, comprising: installing a fixation device in bone, the fixation device comprising a body, a flexible construct formed essentially of a tape with two flexible ends, the flexible construct extending through the body, and a passing device attached to a first of the two flexible ends; and forming, with the flexible construct and the passing device, a knotless closed loop having an adjustable perimeter, after installing the fixation device in the bone, wherein forming the knotless closed loop further comprising forming a splice within the first flexible end, the splice being located within the body of the fixation device.

2. The method of claim 1, further comprising adjusting a length of the knotless closed loop to approximate tissue to bone.

3. The method of claim 1, wherein the tape is a flat construct having a rectangular configuration.

4. The method of claim 1, further comprising: passing the first flexible end around or through tissue to be fixated, and then through an eyelet of the passing device; and pulling on the passing device to allow the first flexible end to form the splice through itself and within the fixation device, and to allow the tape to be positioned around the tissue to be secured, and provide tensioning of the tissue relative to the bone.

5. A method of tissue repair, comprising: providing a surgical device comprising a fixation device and a flexible construct extending through the fixation device, the flexible construct comprising a flexible strand with a suture tape, and a shuttling/pulling device attached to the flexible strand; installing the fixation device into bone; subsequently passing the flexible strand around tissue to be fixated, and then through an eyelet of the shuttling/pulling device so that the suture tape is positioned around the tissue to be fixated; and subsequently pulling on the shuttling/pulling device to allow the flexible strand to form a splice through itself and within the fixation device, and provide tensioning of the tissue to be fixated relative to the bone.

6. The method of claim 5, further comprising: pre-loading the flexible strand onto the fixation device; securing the fixation device to a driver by tying the flexible strand to the driver; threading the shuttling/pulling device through the flexible strand; passing the flexible strand through or around the tissue to be fixated; subsequently, threading the flexible strand through an eyelet of the shuttling/pulling device; and pulling on the shuttling/pulling device to allow the flexible strand to double itself and create the splice within the fixation device.

7. The method of claim 6, wherein the fixation device is a knotless anchor.

8. The method of claim 6, wherein the flexible strand is a suture formed of ultrahigh molecular weight polyethylene.

9. The method of claim 6, wherein the shuttling/pulling device is a suture passer.

\* \* \* \* \*